United States Patent
Gao et al.

(10) Patent No.: US 12,416,556 B2
(45) Date of Patent: Sep. 16, 2025

(54) STRENGTH MEASUREMENT SYSTEM FOR ROCK SPECIMEN UNDER MICROWAVE EFFECT HAVING A TEST CABIN FIXED ON SUPPORTING DEVICE

(71) Applicant: SHENZHEN UNIVERSITY, Shenzhen (CN)

(72) Inventors: Mingzhong Gao, Shenzhen (CN); Bengao Yang, Shenzhen (CN); Xiting Long, Shenzhen (CN); Xiangyue Wen, Shenzhen (CN); Zhaoying Yang, Shenzhen (CN); Xuan Wang, Shenzhen (CN)

(73) Assignee: SHENZHEN UNIVERSITY, Shenzhen (CN)

( * ) Notice: Subject to any disclaimer, the term of this patent is extended or adjusted under 35 U.S.C. 154(b) by 241 days.

(21) Appl. No.: 18/250,291

(22) PCT Filed: Jul. 13, 2021

(86) PCT No.: PCT/CN2021/105969
§ 371 (c)(1),
(2) Date: Apr. 24, 2023

(87) PCT Pub. No.: WO2022/127088
PCT Pub. Date: Jun. 23, 2022

(65) Prior Publication Data
US 2023/0408390 A1    Dec. 21, 2023

(30) Foreign Application Priority Data
Dec. 17, 2020   (CN) .......................... 202011496649.9

(51) Int. Cl.
*G01N 3/12* (2006.01)
*G01N 3/02* (2006.01)
(Continued)

(52) U.S. Cl.
CPC ................. *G01N 3/12* (2013.01); *G01N 3/02* (2013.01); *G01N 2203/0019* (2013.01); *G01N 2203/0048* (2013.01)

(58) Field of Classification Search
CPC .... G01N 3/12; G01N 3/02; G01N 2203/0019; G01N 2203/0048; G01N 22/00;
(Continued)

(56) References Cited

U.S. PATENT DOCUMENTS 6,971,260 B2 * 12/2005 Potter ...................... G01N 3/10
73/152.05
2014/0041940 A1   2/2014 Shnell

FOREIGN PATENT DOCUMENTS

| CN | 204405440 U | 6/2015 |
|----|-------------|--------|
| CN | 106290007 A | 1/2017 |

(Continued)

OTHER PUBLICATIONS

Yin Bangyue, Ceramic Nuclear Fuel Technology, Harbin Engineering University Press, 2015, ISBN 978-7-5661-1004-6, 6 pages.
(Continued)

*Primary Examiner* — Brandi N Hopkins
(74) *Attorney, Agent, or Firm* — MUNCY, GEISSLER, OLDS & LOWE, P.C.

(57) ABSTRACT

A strength measurement system for rock specimen under microwave effect includes a supporting device, a testing cabin, a strength test device, a hydraulic loading device and a microwave transmitting device. Testing cabin is arranged on supporting device; strength test device is arranged in testing cabin, and a rock specimen is arranged on strength test device; a fixed end of hydraulic loading device is arranged on supporting device, and a movable end of hydraulic loading device acts on rock specimen; microwave transmitting device is arranged on testing cabin, and micro- (Continued)

wave transmitting device acts on rock specimen. Testing cabin has isolation function and limits microwave within testing cabin. By loading microwave on rock specimen by means of microwave transmitting device, effect of microwave on rock strength is learnt, and correlation between power and duration of microwave on rock specimen and rock strength is studied in targeted manner.

9 Claims, 6 Drawing Sheets

(51) Int. Cl.
    *G01N 3/10*     (2006.01)
    *G01N 3/18*     (2006.01)
    *G01N 3/24*     (2006.01)

(58) Field of Classification Search
    CPC .. G01N 1/08; G01N 1/44; G01N 3/18; G01N 3/04; G01N 3/303; G01N 3/14; G01N 19/02; G01N 33/24; G01N 1/28; G01N 2203/0256; G01N 2203/0226; G01N 3/08

USPC .................................................. 73/760, 788
See application file for complete search history.

(56) References Cited

FOREIGN PATENT DOCUMENTS

| | | |
|---|---|---|
| CN | 207610921 U | 7/2018 |
| CN | 110749521 A | 2/2020 |
| CN | 111350504 A | 6/2020 |
| CN | 112577829 A | 3/2021 |
| CN | 213903056 U | 8/2021 |
| CN | 214472378 U | 10/2021 |

OTHER PUBLICATIONS

Reigier et al., The microwave processing of food, Second Edition, 2017, Elsevier Ltd. and China Light Industry Press, ISBN 978-0-08-100528-6, 5 pages.

\* cited by examiner

STRENGTH MEASUREMENT SYSTEM FOR ROCK SPECIMEN UNDER MICROWAVE EFFECT HAVING A TEST CABIN FIXED ON SUPPORTING DEVICE

FIELD OF THE APPLICATION

The present application relates to the technical field of equipment in rock mechanics, relates to a strength measurement device, in particular to a measuring device applied to studying rock specimen strength under an effect of microwave.

BACKGROUND

The development of human civilization is inseparably related to a high-efficient utilization of mineral resources, especially since the 1860s, the human have entered industrial revolution, the machine has replaced manpower gradually, becoming an important production resource and production tool, while an operation of the machine is impossible without the mineral resources, therefore, the mineral resources are becoming increasingly scarce. As the mineral resources in the surface layer of the Earth are gradually depleted, exploiting the mineral resources deep under the surface of the Earth tends to be normal.

During exploiting the mineral resources deep under the surface of the Earth, how to crush a rock effectively becomes a research hot spot. A traditional method is mainly performing a rock crush by using a drill bit, however, such an original rock-crushing method, limited by a plurality of factors including an extensive rock strength and an easy wear of the drill bit, and more, has a plurality of problems including a low efficiency and a high cost. In recent years, microwave, due to the advantages of easy to use, rapid in heating, free of a secondary pollution, and more, has been introduced into the rock crush. As a new rock-crushing method, microwave rock crush has achieved a wide attention of scholars in the industry. Several related studies have proven that a microwave effect can reduce the strength of a rock greatly and even lead to rock melting and peeling, and a microwave technology has a good application prospect in the field of the rock crush.

In the prior art, the microwave rock crush is still in a starting stage of research, a correlation between a power duration of the microwave and the rock strength in the field is still not clear, which has restricted seriously a wide application of the microwave rock crush.

BRIEF SUMMARY OF THE DISCLOSURE

According to the defects in the prior art described above, the present application provides a strength measurement system for a rock specimen under a microwave effect, which is helpful for studying the correlation between the power duration of the microwave and the rock strength in a targeted manner, having a great significance to popularizing and applying the microwave technology in the field of rock-crushing.

The technical solution of the present application to solve the technical problem is as follows:

A strength measurement system for a rock specimen under a microwave effect, comprises:
a supporting device;
a testing cabin, the testing cabin is arranged on the supporting device;
a strength test device, the strength test device is arranged in the testing cabin, and the strength test device has a rock specimen arranged thereon;
a hydraulic loading device, a fixed end of the hydraulic loading device is arranged on the supporting device, and a movable end of the hydraulic loading device acts on the rock specimen;
a microwave transmitting device, the microwave transmitting device is arranged on the testing cabin, and the microwave transmitting device acts on the rock specimen.

Compared with the prior art, the present technical solution has a beneficial effect that the correlation between the power duration of the microwave for the rock specimen and the rock strength is studied in a targeted manner, through a cooperation of a plurality of devices including the testing cabin, the strength test device, the microwave transmitting device, and more. On one aspect, by the microwave transmitting device, the microwave is able to be loaded on the rock specimen, thus an effect of the microwave on the rock strength is acknowledged; on another aspect, the testing cabin plays a role for isolation in an extent, limiting the microwave inside the testing cabin.

Further, the supporting device comprises:
a workbench, the workbench is arranged horizontally;
a loading frame, the loading frame is arranged on the workbench fixedly;
a top plate, the top plate is arranged on the loading frame fixedly, and the fixed end of the hydraulic loading device is arranged on the top plate.

A beneficial effect by adopting the solution mentioned above is that, by adopting the workbench, the loading frame, and the top plate to compose the supporting device, a structural supporting effect is achieved, while the testing cabin, the strength test device, the hydraulic loading device, the microwave transmitting device, and more are all arranged on the supporting device directly or indirectly.

Further, the hydraulic loading device comprises:
a longitudinal loading device, the longitudinal loading device is arranged on the loading frame fixedly;
a constant stiffness providing assembly, the constant stiffness providing assembly is arranged fixedly at a lower end of the longitudinal loading device.

A beneficial effect by adopting the solution mentioned above is that, a downward load is provided by means of the longitudinal loading device, and an experimental measurement result is more accurate by ensuring that a pressure applied to the rock specimen tends to be stable by means of the constant stiffness providing assembly.

Further, the testing cabin comprises:
a metal layer cavity and a heat insulation layer cavity, the metal layer cavity and the heat insulation layer cavity both have a cubic cavity structure, while the metal layer cavity is sleeved inside the heat insulation layer cavity, the metal layer cavity and the heat insulation layer cavity form a double-layer structure;
a side door, a side surface of the metal layer cavity and the heat insulation layer cavity has a take-and-place through hole arranged, and the side door is arranged on the take-and-place through hole;
a base, the base is arranged horizontally, located on a bottom surface of the metal layer cavity, and has two guide rails in parallel arranged thereon.

A beneficial effect by adopting the solution mentioned above is that, the metal layer cavity and the heat insulation layer cavity form a double-layer structure, on one aspect, an effect of absorbing the microwaves is achieved, so as to prevent the microwaves in the testing cabin from being radiated out of the testing cabin; and on another aspect, a heat insulation effect can be achieved, so as to ensure a safety of an operator.

Further, the strength test device comprises:
- a strength test upper portion, the strength test upper portion has a loading column penetrating thoroughly arranged, and an upper end of the loading column applies a load downwards under an action of the hydraulic loading device;
- a first strength test lower portion and a second strength test lower portion, the first strength test lower portion and the second strength test lower portion locate under the strength test upper portion, each of the first strength test lower portion and the second strength test lower portion has a guide rail protrusion arranged, both the first strength test lower portion and the second strength test lower portion are arranged movably on the base through a cooperation of the guide rail protrusion and the guide rail.

A beneficial effect by adopting the solution mentioned above is that, by composing a strength test device through the strength test upper portion, the first strength test lower portion, and the second strength test lower portion, after coupling the strength test device with the hydraulic loading device, it is possible to perform a test in a plurality of aspects including tensile strength, compressive strength, shearing strength, and more to the rock specimen, having a plurality of advantages including a simple structure, a wide application range, and more.

Further, the strength test upper portion has a lifting adjustment nut and a lifting adjustment bolt arranged inside, each of the first strength test lower portion and the second strength test lower portion has an inner threaded through hole arranged;

the lifting adjustment bolt penetrates through the strength test upper portion from top down, after being engaged with the lifting adjustment nut, the lifting adjustment bolt is in a threaded fit with the inner threaded through holes in the first strength test lower portion and the second strength test lower portion.

A beneficial effect by adopting the solution mentioned above is that, it is possible to adjust a distance between the strength test upper portion, the first strength test lower portion, and the second strength test lower portion, so as to adapt to the rock specimen having different volumes.

Further, a side surface of the first strength test lower portion has a first horizontal adjustment screw arranged, the first horizontal adjustment screw is in a threaded fit with a first horizontal adjustment nut arranged on a side surface of the testing cabin, the first horizontal adjustment screw penetrates through the side surface of the testing cabin before connecting fixedly to the first strength test lower portion, the first horizontal adjustment screw is applied to adjusting a horizontal movement of the first strength test lower portion along the guide rail;

a side surface of the second strength test lower portion has a second horizontal adjustment screw arranged, the second horizontal adjustment screw is in a threaded fit with a second horizontal adjustment nut arranged on a side surface of the testing cabin, the second horizontal adjustment screw penetrates through the side surface of the testing cabin before connecting fixedly to the second strength test lower portion, the second horizontal adjustment screw is applied to adjusting a horizontal movement of the second strength test lower portion along the guide rail.

A beneficial effect by adopting the solution mentioned above is that, adjusting a distance between the first strength test lower portion and the second strength test lower portion by the first horizontal adjustment screw and the second horizontal adjustment screw, so as to perform a Brazilian splitting test to the rock specimen having a different volume.

Further, a lower surface of the strength test upper portion has an upper groove arranged, an upper surface of the first strength test lower portion has a first lower groove arranged, an upper surface of the second strength test lower portion has a second lower groove arranged, the first lower groove and the second lower groove locate below the upper groove;

a test fixture is further arranged between the strength test upper portion, the first strength test lower portion, and the second strength test lower portion, the test fixture locates between the upper groove, the first lower groove and the second lower groove, a center of the test fixture has a force transmission cushion block and a hemispherical seat arranged from top down, an upper end of the force transmission cushion block abuts against a lower end of the loading column, a lower end of the force transmission cushion block abuts against an upper end of the hemispherical seat, and a lower end of the hemispherical seat is exposed out of the test fixture;

the strength test upper portion has a fastening bolt arranged, the fastening bolt penetrates through the strength test upper portion before fixing the test fixture below the strength test upper portion.

A beneficial effect by adopting the solution mentioned above is that, it facilitates the Brazilian splitting test.

Further, the base has a bottom support recess arranged, the bottom support recess locates between two of the guide rails, and the bottom support recess locates directly below the loading column.

Further, the microwave transmitting device comprises a microwave source, a coupler, a circulator, a water load, a waveguide tube, and a microwave emitting plate;

the microwave source couples with one end of the waveguide tube through the coupler, another end of the waveguide tube connects to one end of the circulator, another end of the circulator connects to the microwave emitting plate, and the microwave emitting plate faces to the rock specimen inside the strength test device.

A beneficial effect by adopting the solution mentioned above is that, by the microwave transmission device composed of the microwave source, the coupler, the circulator, the water load, the waveguide tube, and the microwave emitting plate, it is possible to load the microwave onto the rock specimen.

Wherein, 1—supporting device, 2—testing cabin, 3—strength test device, 4—hydraulic loading device, 5—microwave transmitting device;
101—workbench, 102—loading frame, 103—top plate;
201—metal layer cavity, 202—heat insulation layer cavity, 203—base, 204—guide rail;
301—strength test upper portion, 302—loading column, 303—first strength test lower portion, 304—second strength test lower portion, 305—guide rail protrusion, 306—lifting adjustment nut, 307—lifting adjustment bolt, 308—first horizontal adjustment screw, 309—first horizontal adjustment nut, 310—second horizontal adjustment screw, 311—second horizontal adjustment nut, 312—test fixture, 313—force transmission cushion block, 314—hemispherical seat, 315—fastening bolt, 316—bottom support recess;
401—longitudinal loading device, 402—constant stiffness providing assembly;
501—microwave source, 502—coupler, 503—circulator, 504—water load, 505—waveguide tube, 506—microwave emitting plate.

DETAILED DESCRIPTION OF EMBODIMENTS

In order to make the purpose, technical solution, and the advantages of the present application clearer and more explicit, further detailed descriptions of the present application are stated herein, referencing to the attached drawings and some embodiments of the present application. It should be understood that the detailed embodiments of the application described here are used to explain the present application only, instead of limiting the present application.

In the description of the present application, it should be understood that the orientation or positional relationship indicated by the terms "center," "upper," "lower," "front," "rear," "left," "right," and the like is based on the orientation or positional relationship shown in the drawings, and is merely intended to facilitate the description of the application and to simplify the description, rather than to indicate or imply that the indicated device or component must have a particular orientation, constructed and operated in a particular orientation, and therefore cannot be understood as a limitation to the present application. In addition, the terms "first" and "second" are used for descriptive purposes only and cannot be understood as indicating or implying relative importance.

In the description of the present application, unless expressly specified and defined otherwise, the terms "mounted", "connected" and "connected" shall be understood broadly, for example, may be a fixed connection, a detachable connection, or an integrated connection; may be a mechanical connection or an electrical connection; may be directly connected, or may be indirectly connected by means of an intermediate medium, and may be an internal communication between the two components. When the component is referred to as being "fixed to" or "disposed to" another component, the component may be directly on the another component or there may also be intermediate components between the component and the another component. When one component is considered to be "connected" another component, the component may be directly connected to the another component or there may be intermediate components between the component and the another component at the same time. For a person of ordinary skills in the art, the specific meanings of the above terms in the present application may be understood according to specific conditions.

During exploiting the mineral resources deep under the surface of the Earth, how to crush a rock effectively becomes a research hot spot. A traditional method is mainly performing a rock crush by using a drill bit, however, such an original rock-crushing method, limited by a plurality of factors including an extensive rock strength and an easy wear of the drill bit, and more, has a plurality of problems including a low efficiency and a high cost. In recent years, microwave, due to having a plurality of advantages including easy to use, rapid in heating, free of a secondary pollution and more, has been introduced into the rock crush. As a new rock-crushing method, microwave rock crush has achieved a wide attention of scholars in the industry. A plurality of related studies have proven that a microwave effect can reduce the strength of a rock greatly and even lead to rock melting and peeling, and a microwave technology has a good application prospect in the field of the rock crush.

Before promoting a new technology on the microwave rock crush, an influence of the microwave acting on the rock strength must be studied in details, in a scientific and systematic way. In the prior art, the microwave rock crush is still in a starting stage of research, a correlation between a power duration of the microwave and the rock strength in the field is still not clear, which has restricted seriously a wide application of microwave rock-crushing.

Figure 1:
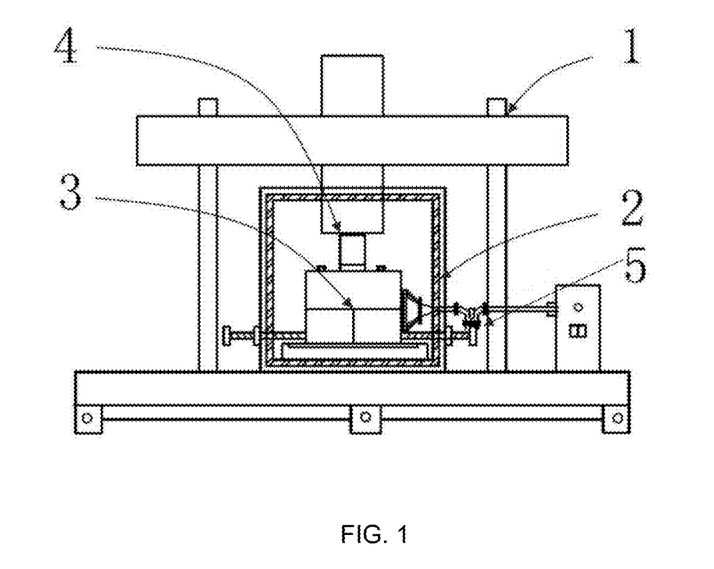
FIG. 1 illustrates an overall schematic diagram on a strength measurement system for a rock specimen under a microwave effect according to the present application.

Shown as FIG. 1, in order to solve the problem stated above, the present application provides a strength measurement system for a rock specimen under a microwave effect, comprising a supporting device 1, a testing cabin 2, a strength test device 3, a hydraulic loading device 4, and a microwave transmitting device 5. A function of the supporting device 1 is providing a structural support to the strength measurement system for the rock specimen under the microwave effect in a whole, while a function of the hydraulic loading device 4 is providing a load to measure a strength change of the rock specimen after a microwave effect.

Specifically, the present application, wherein the strength measurement system for the rock specimen further comprises the testing cabin 2, the strength test device 3, and the microwave transmitting device 5. The strength test device 3 has a plurality of testing functions integrated including a tensile strength, a compressive strength, a shearing strength, and more; the microwave transmitting device 5 is able to transmit a microwave and load the microwave on the rock specimen; while the testing cabin 2 is applied to providing a relatively closed space, and preventing the microwave from affecting an external environment.

The testing cabin 2 is arranged on the supporting device 1; the strength test device 3 is arranged in the testing cabin 2, and the strength test device 3 has a rock specimen arranged thereon; a fixed end of the hydraulic loading device 4 is arranged on the supporting device 1, and a movable end of the hydraulic loading device 4 acts on the rock specimen; the microwave transmitting device 5 is arranged on the testing cabin 2, and the microwave transmitting device 5 acts on the rock specimen. Through a cooperation of a plurality of devices including the testing cabin 2, the strength test device 3, the microwave transmitting device 5 and more, a correlation between a power duration of the microwave for the rock specimen and a rock strength is studied in a targeted manner. On one hand, by the microwave transmitting device 5, the microwave is able to be loaded on the rock specimen, thus an effect of the microwave on the rock strength is acknowledged; on another hand, the testing cabin 2 plays a role for isolation in an extent, limiting the microwave inside the testing cabin 2.

Figure 2:
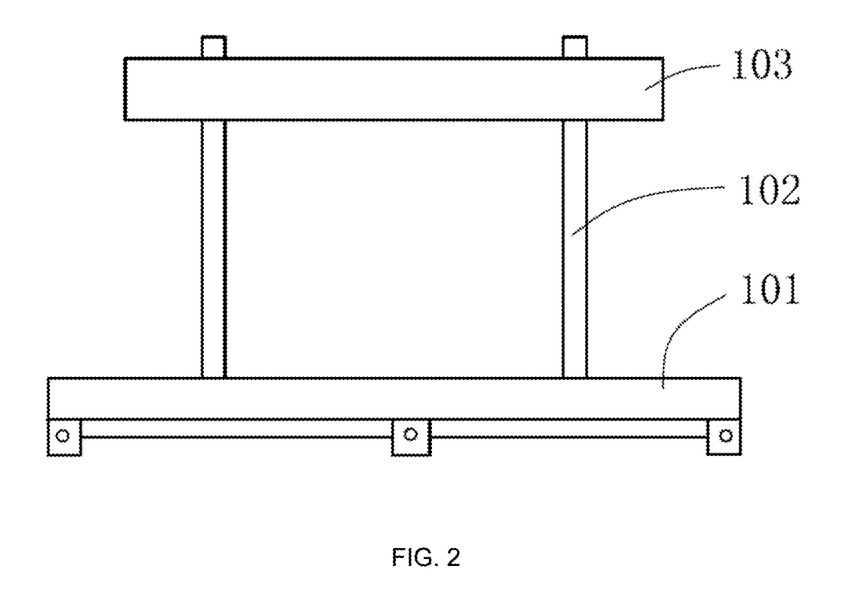
FIG. 2 illustrates a schematic diagram on a supporting device in a strength measurement system for a rock specimen under a microwave effect according to the present application.

Shown as FIG. 2, specifically, the supporting device 1 comprises a workbench 101, a loading frame 102 and a top plate 103; the workbench 101 is arranged horizontally, the loading frame 102 is arranged on the workbench 101 fixedly, the top plate 103 is arranged on the loading frame 102 fixedly, and the fixed end of the hydraulic loading device 4 is arranged on the top plate 103. By adopting the workbench 101, the loading frame 102 and the top plate 103 to compose the supporting device 1, a structural supporting effect is achieved, while the testing cabin 2, the strength test device 3, the hydraulic loading device 4, the microwave transmitting device 5 and more are all arranged on the supporting device 1 directly or indirectly, composing an integral structure.

Figure 3:
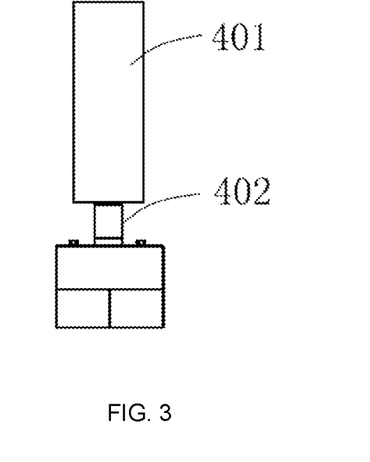
FIG. 3 illustrates a schematic diagram on a hydraulic loading device in a strength measurement system for a rock specimen under a microwave effect according to the present application.

Shown as FIG. 1 and FIG. 3, the hydraulic loading device 4 comprises a longitudinal loading device 401 and a constant stiffness providing assembly 402; the longitudinal loading device 401 is arranged on the loading frame 102 fixedly; the constant stiffness providing assembly 402 is arranged fixedly at a lower end of the longitudinal loading device 401. The longitudinal loading device 401 locates above the testing cabin 2, the lower end of the longitudinal loading device 401 connects to the constant stiffness providing assembly 402, and the constant stiffness providing assembly 402 connects to a loading column 302 in the strength test device 3. By providing a downward load by means of the longitudinal loading device 401, and by ensuring that a pressure applied to the rock specimen tends to be stable by means of the constant stiffness providing assembly 402, an experimental measurement result is more accurate and reliable Shown as FIG. 4, the testing cabin 2 comprises a metal layer cavity 201, a heat insulation layer cavity 202 and a base 203; wherein both the metal layer cavity 201 and the heat insulation layer cavity 202 are having a cubic cavity structure, while the metal layer cavity 201 is sleeved inside the heat insulation layer cavity 202, the metal layer cavity 201 and the heat insulation layer cavity 202 are forming a double-layer structure. In addition, a side surface of the metal layer cavity 201 and the heat insulation layer cavity 202 has a take-and-place through hole arranged, and a side door is arranged on the take-and-place through hole. The testing cabin 2 is fixed on the workbench 101, a cabin body of the testing cabin 2 is a double-layer structure, an inner layer is made of a metal material such as an aluminum alloy, and an outer layer is made of a heat insulation material such as a glass wool; and one side of the testing cabin 2 has a side door being able to be opened or closed arranged, facilitating to take or place the rock specimen, and adjust the strength test device 3. The metal layer cavity 201 and the heat insulation layer cavity 202 are forming a double-layer structure, so that on one hand, an effect of absorbing the microwaves is achieved, so as to prevent the microwaves in the testing cabin 2 from being radiated to an outside of the testing cabin 2; and on another hand, a heat insulation effect can be achieved, so as to insure a safety of an operator.

Figure 4:
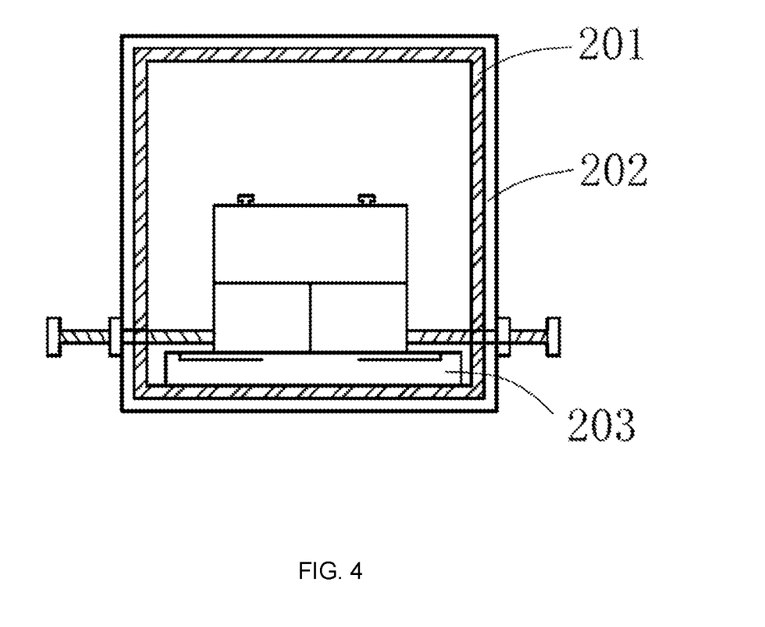
FIG. 4 illustrates a schematic diagram on a testing cabin in a strength measurement system for a rock specimen under a microwave effect according to the present application.
Figure 5:
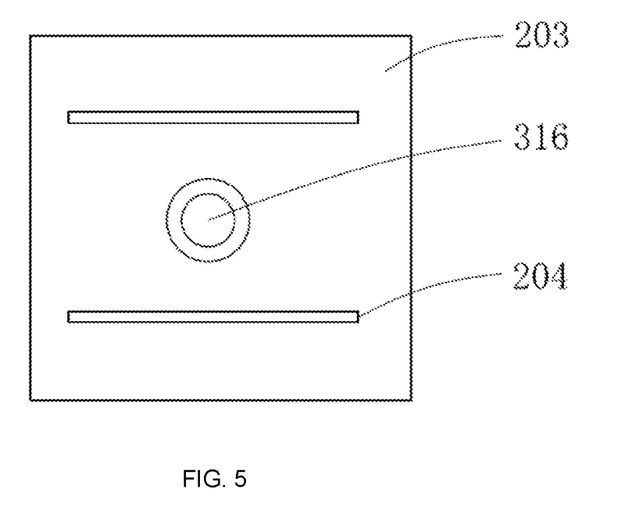
FIG. 5 illustrates a schematic diagram on a base in a strength measurement system for a rock specimen under a microwave effect according to the present application.

Shown as FIG. 4 and FIG. 5, the base 203 is arranged horizontally, located on a bottom surface of the metal layer cavity 201, and having two guide rails 204 in parallel arranged thereon. In short, the testing cabin 2 has the base 203 fixed inside, the base 203 has the guide rails 204 and a bottom support recess 316 performing a compressive strength measurement arranged, the bottom support recess 316 locates between two of the guide rails 204, and the bottom support recess 316 locates directly below the loading column 302. By arranging the bottom support recess 316 between two of the guide rails 204, it is more convenient to perform the compressive strength measurement.

Figure 6:
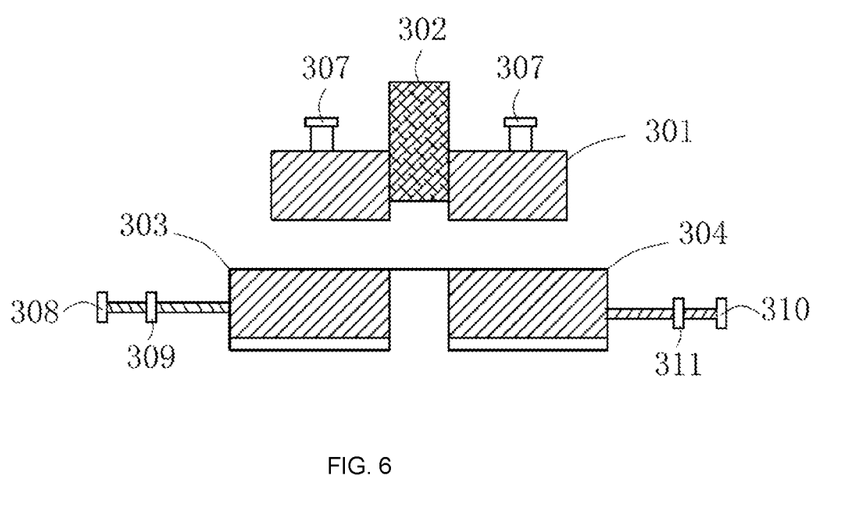
FIG. 6 illustrates a schematic diagram on a strength test device in a strength measurement system for a rock specimen under a microwave effect according to the present application.

Shown as FIG. 6, the strength test device 3 comprises a strength test upper portion 301, a first strength test lower portion 303 and a second strength test lower portion 304. The strength test upper portion 301 has a loading column 302 arranged penetrating thoroughly, and an upper end of the loading column 302 applies a load downwards under an action of the hydraulic loading device 4; the first strength test lower portion 303 and the second strength test lower portion 304 locate under the strength test upper portion 301, each of the first strength test lower portion 303 and the second strength test lower portion 304 has a guide rail protrusion 305 arranged, both the first strength test lower portion 303 and the second strength test lower portion 304 are arranged movably on the base 203 through a cooperation of the guide rail protrusions 305 and the guide rails 204. The first strength test lower portion 303 and the second strength test lower portion 304 connect to the guide rails 204 through the guide rail protrusions 305, so as to placing a test equipment on the base 203 stably.

Generally, a method for measuring the strength of a rock mainly comprises single-axis anti-compression, Brazil splitting, double-sided shearing, and more, to perform a plurality of tests including tensile strength test, compressive strength test, shearing strength test, and more, while each method requires to correspond to a different measuring device. By the strength test upper portion 301, the first strength test lower portion 303, and the second strength test lower portion 304 composing the strength test device 3, after connecting with the hydraulic loading device 4, it is able to perform a plurality of tests including tensile strength test, compressive strength test, shearing strength test, and more, having a plurality of advantages including a simple structure, a wide application range and more.

Figure 8:
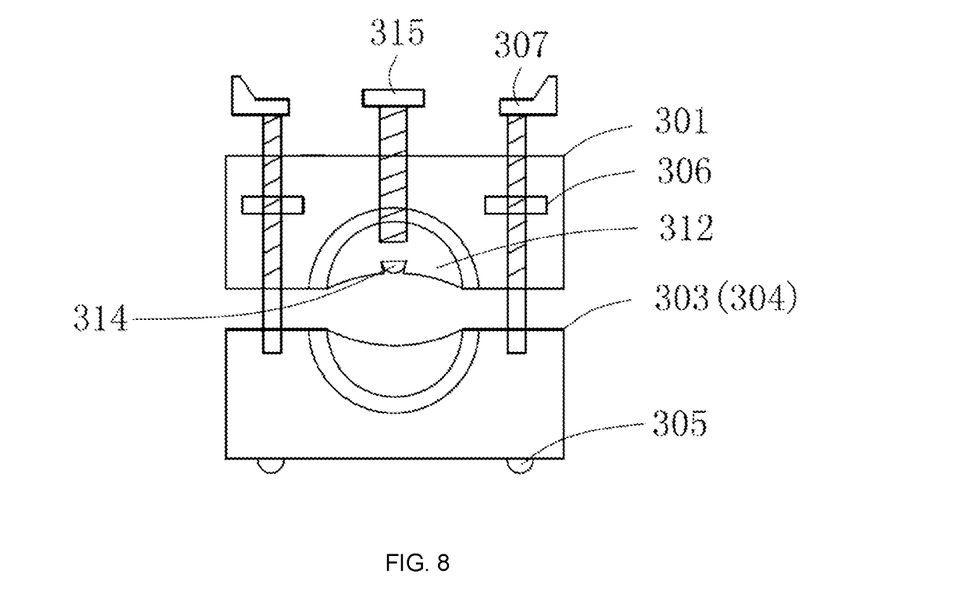
FIG. 8 illustrates a schematic diagram on a strength test upper portion and a first strength test lower portion or a second strength test lower portion in a strength measurement system for a rock specimen under a microwave effect according to the present application.

Shown as FIG. 6 and FIG. 8, the strength test upper portion 301 has a lifting adjustment nut 306 and a lifting adjustment bolt 307 arranged inside, each of the first strength test lower portion 303 and the second strength test lower portion 304 has an inner threaded through hole arranged; the lifting adjustment bolt 307 penetrates through the strength test upper portion 301 from top down, after being engaged on the lifting adjustment nut 306, the lifting adjustment bolt 307 is in a threaded fit with the inner threaded through holes in the first strength test lower portion 303 and the second strength test lower portion 304. By adopting the lifting adjustment nut 306 and the lifting adjustment bolt 307, it is possible to adjust a distance between the strength test upper portion 301, and the first strength test lower portion 303 and the second strength test lower portion 304, so as to adapt to the rock specimen having a different volume.

Figure 7:
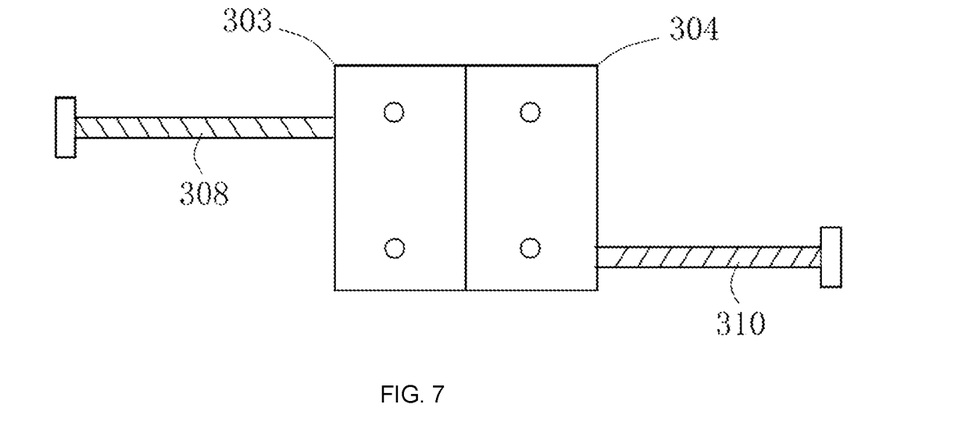
FIG. 7 illustrates a schematic diagram on a first horizontal adjustment screw and a second horizontal adjustment screw in a strength measurement system for a rock specimen under a microwave effect according to the present application.

Shown as FIG. 1, FIG. 6 and FIG. 7, a side surface of the first strength test lower portion 303 has a first horizontal adjustment screw 308 arranged, the first horizontal adjustment screw 308 is in a threaded fit with a first horizontal adjustment nut 309 arranged on a side surface of the testing cabin 2, the first horizontal adjustment screw 308 penetrates through the side surface of the testing cabin 2 before connecting fixedly to the first strength test lower portion 303, the first horizontal adjustment screw 308 is applied to adjusting a horizontal movement of the first strength test lower portion 303 along the guide rail 204. Accordingly, a side surface of the second strength test lower portion 304 has a second horizontal adjustment screw 310 arranged, the second horizontal adjustment screw 310 is in a threaded fit with a second horizontal adjustment nut 311 arranged on a side surface of the testing cabin 2, the second horizontal adjustment screw 310 penetrates through the side surface of the testing cabin 2 before connecting fixedly to the second strength test lower portion 304, the second horizontal adjustment screw 310 is applied to adjusting a horizontal movement of the second strength test lower portion 304 along the guide rail 204.

A strength test lower portion is divided into two portions, individually, they are the first strength test lower portion 303 and the second strength test lower portion 304, and each portion is connected with a screw extending out of the testing cabin 2. By moving the screw outside the testing cabin 2, a position of a lower part of a test device can be adjusted, so as to perform a tensile, compress and shear test to the specimen respectively. In an embodiment, when performing a Brazil splitting test, a rock specimen needs to be placed horizontally, while a rock specimen having a different volume has a different projection coverage range in a horizontal direction. In order to adapt to more rock specimens, a distance between the first strength test lower portion 303 and the second strength test lower portion 304 is adjusted by the first horizontal adjustment screw 308 and the second horizontal adjustment screw 310, so as to apply the Brazilian splitting test to the rock specimens having different volumes.

In addition, arranging the first horizontal adjusting nut 309 and the second horizontal adjusting nut 311 outside a cabin, and after adjusting a relative position between the first strength test lower portion 303 and the second strength test lower portion 304 through the first horizontal adjusting screw 308 and the second horizontal adjusting screw 310, the relative positions of the first strength test lower portion 303 and the second strength test lower portion 304 can be fixed by tightening the first horizontal adjusting nut 309 and the second horizontal adjusting nut 311, while isolating a gap between a screw and the cabin body, so as to ensure sealing a cavity.

Shown as FIG. 8, a lower surface of the strength test upper portion 301 has an upper groove arranged, an upper surface of the first strength test lower portion 303 has a first lower groove arranged, an upper surface of the second strength test lower portion 304 has a second lower groove arranged, the first lower groove and the second lower groove locate below the upper groove. Accordingly, a test fixture 312 is further arranged between the strength test upper portion 301, and the first strength test lower portion 303 and the second strength test lower portion 304, the test fixture 312 locates between the upper groove, the first lower groove and the second lower groove.

Figure 9:
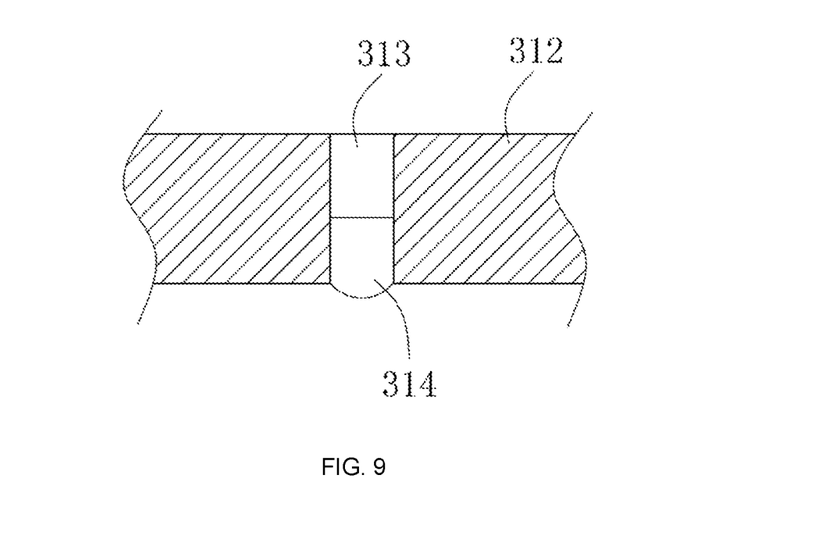
FIG. 9 illustrates a schematic diagram on a test fixture in a strength measurement system for a rock specimen under a microwave effect according to the present application.

Shown as FIG. 9, a center of the test fixture 312 has a force transmission cushion block 313 and a hemispherical seat 314 arranged from top down, an upper end of the force transmission cushion block 313 abuts against a lower end of the loading column 302, a lower end of the force transmission cushion block 313 abuts against an upper end of the hemispherical seat 314, and a lower end of the hemispherical seat 314 is exposed out of the test fixture 312. In addition, the strength test upper portion 301 has a fastening bolt 315 arranged, the fastening bolt 315 penetrates through the strength test upper portion 301 before fixing the test fixture 312 below the strength test upper portion 301.

The strength test upper portion 301 has the test fixture 312 arranged, and the fastening bolt 315 arranged in a center of both sides, it is possible to fix the rock specimen placed in a test device, and fix a test mold used for a different test. When performing a shearing test, the strength test device 3 has different aperture molds arranged; when performing a tensile strength test, a test fixture 312 required is arranged, and the test fixture 312 has a force transmission cushion block 313 arranged, the force transmission cushion block 313 has a hemispherical seat 314 arranged below, and during loading, the rock specimen is fractured by the hemispherical seat 314. Therefore, a structural arrangement stated above facilitates the Brazilian splitting test.

Figure 10:
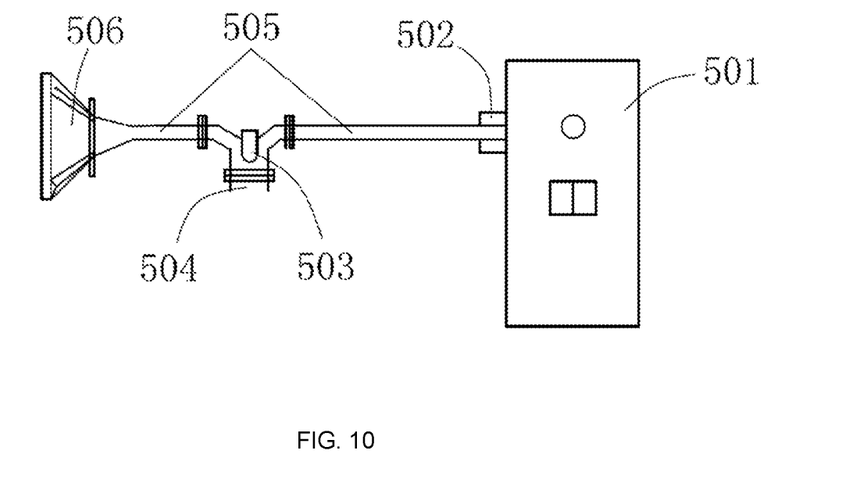
FIG. 10 illustrates a schematic diagram on a microwave transmitting device in a strength measurement system for a rock specimen under a microwave effect according to the present application.

Shown as FIG. 10, the microwave transmitting device 5 comprises a microwave source 501, a coupler 502, a circulator 503, a water load 504, a waveguide tube 505, and a microwave emitting plate 506; the microwave source 501 couples with one end of the waveguide tube 505 through the coupler 502, another end of the waveguide tube 505 connects to one end of the circulator 503, another end of the circulator 503 connects to the microwave emitting plate 506, and the microwave emitting plate 506 faces to the rock specimen inside the strength test device 3.

The microwave transmitting device 5 is composed by a microwave source 501, a coupler 502, a circulator 503, a water load 504, a waveguide tube 505, and a microwave emitting plate 506. The microwave source 501 converts electrical energy into microwave energy, and propagates the microwave energy to the circulator 503 through the coupler 502 and the waveguide tube 505; the circulator 503 has the water load 504 connected below, and then the microwave energy is transmitted into the testing cabin 2 through the waveguide tube 505. The microwave is directed to and affects the rock specimen in the strength test device 3, after changing an irradiation position by a microwave reflecting plate having an angle-adjustable end. In the present technical solution, a power of the microwave emission source is adjustable, so as to output a microwave having a different power as required. Through the microwave transmitting device 5 composed of the microwave source 501, the coupler 502, the circulator 503, the water load 504, the waveguide tube 505, and the microwave emitting plate 506, it is possible to load the microwave onto the rock specimen.

When performing a microwave shearing test by using a double-sided shearing method implemented by the strength measurement system for the rock specimen under the microwave effect, a specific operation step is as follows:

S1: opening the testing cabin 2, adjusting the first strength test lower portion 303 and the second strength test lower portion 304 to an appropriate position by using the first horizontal adjustment screw 308 and the second horizontal adjustment screw 310, to leave a space required for shearing a sample; tightening and fixing the first horizontal adjustment nut 309 and the second horizontal adjustment nut 311 after an appropriate adjustment.

S2: selecting a loading mold of the strength test device 3 according to a size of the rock specimen. Placing the rock specimen into a test hole of the strength test device 3, adjusting the lifting adjustment bolt 307 and fixing the strength test upper portion 301 to a suitable position, making the loading column 302 in the strength test upper portion 301 connect to the constant stiffness providing assembly 402 in the hydraulic loading device 4.

S3: tightening the fastening bolt 315 in the strength test upper portion 301, to fix the mold and the rock specimen having been being loaded. Adjusting an angle of the microwave reflecting plate to ensure that the microwave irradiates directly on the rock specimen, before closing the testing cabin 2.

S4: turning on a microwave emission source to perform a microwave effect on the rock specimen at a different frequency or a different intensity or a different duration.

S5: turning on the longitudinal loading device 401, performing a loading and shearing test on the rock specimen, a stress sensor on the longitudinal loading device 401 transmitting pressure data to a data collection end, so as to obtain a shearing strength of the rock specimen under an effect of the microwave.

When performing a compressive strength test by using a single-axis anti-compression method implemented by the strength measurement system for the rock specimen under the microwave effect, a specific operation step is as follows:

S1: opening the testing cabin 2, adjusting the first strength test lower portion 303 and the second strength test lower portion 304 to an appropriate position by using the first horizontal adjustment screw 308 and the second horizontal adjustment screw 310, to leave a space required for a compressive strength sample; tightening and fixing the first horizontal adjustment nut 309 and the second horizontal adjustment nut 311 after an appropriate adjustment.

S2: placing the rock specimen on the base 203 below the strength test device 3, adjusting the lifting adjustment bolt 307 and fixing the strength test upper portion 301 to a suitable position, before connecting the loading column 302 in the strength test upper portion 301 to the constant stiffness providing assembly 402 below the longitudinal loading device 401.

S3: adjusting an angle of the microwave reflecting plate to ensure that the microwave irradiates directly on the rock specimen, before closing the testing cabin 2.

S4: turning on a microwave emission source to perform a microwave effect on the rock specimen at a different frequency or a different intensity or a different duration.

S5: turning on the longitudinal loading device 401, performing a loading and tensile strength test on the rock specimen, a stress sensor on the longitudinal loading device 401 transmitting pressure data to a data collection end, so as to obtain a compressive strength of the rock specimen under the effect of the microwave.

When performing a tensile strength test by using a Brazilian splitting method implemented by the strength measurement system for the rock specimen under the microwave effect, a specific operation step is as follows:

S1: opening the testing cabin 2, adjusting the first strength test lower portion 303 and the second strength test lower portion 304 to an appropriate position by using the first horizontal adjustment screw 308 and the second horizontal adjustment screw 310, to make both upper and lower portions of the test device abut; tightening and fixing the first horizontal adjustment nut 309 and the second horizontal adjustment nut 311 after an appropriate adjustment.

S2: selecting a loading mold of the strength test device 3 according to a size of the rock specimen. Selecting a test fixture 312 required by a tensile strength test, placing the rock specimen into a test hole of the strength test device 3, adjusting the lifting adjustment bolt 307 and fixing the strength test upper portion 301 to a suitable position, until the strength test upper portion 301 being close to the rock specimen without any loads applied. Then connecting the loading column 302 in the strength test upper portion 301 to the constant stiffness providing assembly 402 on the longitudinal loading device 401.

S3: tightening the fastening bolt 315 in the strength test upper portion 301, to fix the mold having been being loaded. Adjusting an angle of the microwave reflecting plate to ensure that the microwave irradiates directly on the rock specimen, before closing the testing cabin 2.

S4: turning on a microwave emission source to perform a microwave effect on the rock specimen at a different frequency or a different intensity or a different duration.

S5: turning on the longitudinal loading device 401, performing a loading test on the rock specimen, a stress sensor on the longitudinal loading device 401 transmitting pressure data to a data collection end, so as to obtain a tensile strength of the rock specimen under the effect of the microwave.

All above, the present application provides a strength measurement system for a rock specimen under a microwave effect, mainly comprising a hydraulic loading device 4, a microwave transmitting device 5, a testing cabin 2, a strength test device 3, and more. Compared with the prior art, the present technical solution has a plurality of beneficial effects as below: integrating the microwave transmitting device 5 and the strength test device 3 together, it is possible to test and measure a strength change of the rock specimen under an effect of the microwave, before obtaining an influence of the microwave having different powers and different durations on a property of the rock specimen. By integrating a plurality of measuring devices together to measure the tensile strength, compressive strength, and shearing strength of the rock specimen, the strength measurement system has a plurality of characters including a small volume, a simple operation, an easy installation and more, which is suitable for an indoor or an on-site test. By changing the positions of an upper portion and a lower portion of the strength test device 3 through a screw, and selecting different loading molds, it is possible to achieve a strength test to the rock specimen having different sizes and different shapes, so that most rock specimens are able to be tested.

It should be understood that, the application of the present application is not limited to the above embodiments listed. A person of those skills in the art can improve or change the application according to the above descriptions, all of these improvements and transforms should belong to the scope of protection in the appended claims of the present application.

What is claimed is:

1. A strength measurement system for a rock specimen under microwave effect, comprising:
   a supporting device;

a testing cabin, the testing cabin is arranged on the supporting device;

a strength test device, the strength test device is arranged in the testing cabin, and a rock specimen is arranged on the strength test device;

a hydraulic loading device, a fixed end of the hydraulic loading device is arranged on the supporting device, and a movable end of the hydraulic loading device acts on the rock specimen;

a microwave transmitting device, the microwave transmitting device is arranged on the testing cabin, and the microwave transmitting device acts on the rock specimen;

wherein the testing cabin comprises:

a metal layer cavity and a heat insulation layer cavity, both the metal layer cavity and the heat insulation layer cavity have a cubic cavity structure, the metal layer cavity is sleeved inside the heat insulation layer cavity, the metal layer cavity and the heat insulation layer cavity form a double-layer structure;

a side door, a side surface of the metal layer cavity and the heat insulation layer cavity has a take-and-place through hole arranged, and the side door is arranged on the take-and-place through hole;

a base, the base is arranged horizontally, and is located on a bottom surface of the metal layer cavity, and two guide rails in parallel are arranged on the base.

2. The strength measurement system according to claim 1, wherein the supporting device comprises:

a workbench, the workbench is arranged horizontally;

a loading frame, the loading frame is arranged on the workbench fixedly;

a top plate, the top plate is arranged on the loading frame fixedly, and the fixed end of the hydraulic loading device is arranged on the top plate.

3. The strength measurement system according to claim 2, wherein the hydraulic loading device comprises:

a longitudinal loading device, the longitudinal loading device is arranged on the loading frame fixedly;

a constant stiffness providing assembly, the constant stiffness providing assembly is arranged fixedly at a lower end of the longitudinal loading device.

4. The strength measurement system according to claim 1, wherein, the microwave transmitting device comprises a microwave source, a coupler, a circulator, a water load, a waveguide tube, and a microwave emitting plate;

the microwave source couples with one end of the waveguide tube through the coupler, another end of the waveguide tube connects to one end of the circulator, another end of the circulator connects to the microwave emitting plate, and the microwave emitting plate faces to the rock specimen inside the strength test device.

5. The strength measurement system according to claim 1, wherein the strength test device comprises:

a strength test upper portion, the strength test upper portion has a loading column penetrating thoroughly arranged, and an upper end of the loading column applies a load downwards under an action of the hydraulic loading device;

a first strength test lower portion and a second strength test lower portion, the first strength test lower portion and the second strength test lower portion locate under the strength test upper portion, each of the first strength test lower portion and the second strength test lower portion has a guide rail protrusion arranged, both the first strength test lower portion and the second strength test lower portion are arranged movably on the base through a cooperation of the guide rail protrusion and the guide rail.

6. The strength measurement system according to claim 5, wherein the strength test upper portion has a lifting adjustment nut and a lifting adjustment bolt arranged inside, each of the first strength test lower portion and the second strength test lower portion has an inner threaded through hole arranged;

the lifting adjustment bolt penetrates through the strength test upper portion from top down, after being engaged with the lifting adjustment nut, the lifting adjustment bolt is in a threaded fit with the inner threaded through holes in the first strength test lower portion and the second strength test lower portion.

7. The strength measurement system according to claim 5, wherein a side surface of the first strength test lower portion has a first horizontal adjustment screw arranged, the first horizontal adjustment screw is in a threaded fit with a first horizontal adjustment nut arranged on a side surface of the testing cabin, the first horizontal adjustment screw penetrates through the side surface of the testing cabin before connecting fixedly to the first strength test lower portion, the first horizontal adjustment screw is applied to adjusting a horizontal movement of the first strength test lower portion along the guide rail;

a side surface of the second strength test lower portion has a second horizontal adjustment screw arranged, the second horizontal adjustment screw is in a threaded fit with a second horizontal adjustment nut arranged on a side surface of the testing cabin, the second horizontal adjustment screw penetrates through the side surface of the testing cabin before connecting fixedly to the second strength test lower portion, the second horizontal adjustment screw is applied to adjusting a horizontal movement of the second strength test lower portion along the guide rail.

8. The strength measurement system according to claim 5, wherein a lower surface of the strength test upper portion has an upper groove arranged, an upper surface of the first strength test lower portion has a first lower groove arranged, an upper surface of the second strength test lower portion has a second lower groove arranged, the first lower groove and the second lower groove locate below the upper groove;

a test fixture is further arranged between the strength test upper portion, the first strength test lower portion, and the second strength test lower portion, the test fixture is located between the upper groove, the first lower groove, and the second lower groove, a center of the test fixture has a force transmission cushion block and a hemispherical seat arranged from top down, an upper end of the force transmission cushion block abuts against a lower end of the loading column, a lower end of the force transmission cushion block abuts against an upper end of the hemispherical seat, and a lower end of the hemispherical seat is exposed out of the test fixture;

the strength test upper portion has a fastening bolt arranged, the fastening bolt penetrates through the strength test upper portion before fixing the test fixture below the strength test upper portion.

9. The strength measurement system according to claim 5, wherein the base has a bottom support recess arranged, the bottom support recess locates between two guide rails, and the bottom support recess locates directly below the loading column.

* * * * *